United States Patent [19]
Wingrove

[11] Patent Number: 5,540,735
[45] Date of Patent: Jul. 30, 1996

[54] APPARATUS FOR ELECTRO-STIMULATION OF FLEXING BODY PORTIONS

[75] Inventor: Robert C. Wingrove, Inver Grove Heights, Minn.

[73] Assignee: Rehabilicare, Inc., St. Paul, Minn.

[21] Appl. No.: 353,674

[22] Filed: Dec. 12, 1994

[51] Int. Cl.$^6$ ............................. A61N 1/32; A01F 5/04
[52] U.S. Cl. .................... 607/46; 607/2; 607/48; 602/21
[58] Field of Search .................. 607/2, 46, 48, 607/59, 61, 62, 66, 67–74, 149, 55, 144, 152, 153; 128/739, 741, 742, 744, 879, 898; 602/21, 64

[56] References Cited

U.S. PATENT DOCUMENTS

| | | |
|---|---|---|
| 1,545,413 | 7/1925 | Elmvall . |
| 3,845,771 | 11/1974 | Vice . |
| 3,895,639 | 7/1975 | Rodker . |
| 3,911,910 | 10/1975 | Oesau . |
| 4,018,218 | 4/1977 | Carlson et al. . |
| 4,207,904 | 6/1980 | Greene . |
| 4,305,402 | 12/1981 | Katims ............................ 607/66 |
| 4,510,939 | 4/1985 | Brenman et al. . |
| 4,541,432 | 9/1985 | Molina-Negro et al. ............ 607/46 |
| 4,580,569 | 4/1986 | Petrofsky . |
| 4,664,118 | 5/1987 | Batters ............................ 607/46 |
| 4,834,079 | 5/1989 | Benckhuijsen . |
| 4,909,255 | 3/1990 | Farin . |
| 4,915,097 | 4/1990 | West ............................ 602/21 |
| 4,982,742 | 1/1991 | Claude . |
| 4,989,605 | 2/1991 | Rossen ............................ 607/46 |
| 5,000,178 | 3/1991 | Griffith . |
| 5,014,689 | 5/1991 | Meunchen et al. ............ 602/21 |
| 5,022,390 | 6/1991 | Whiteside ............................ 607/2 |
| 5,067,478 | 11/1991 | Berlant . |
| 5,100,373 | 3/1992 | Liboff et al. . |
| 5,123,413 | 6/1992 | Hasegawa et al. . |
| 5,161,530 | 11/1992 | Gamble ............................ 607/67 |
| 5,256,136 | 10/1993 | Sucher ............................ 602/21 |
| 5,279,545 | 1/1994 | Reese, Sr. ............................ 602/21 |
| 5,324,317 | 6/1994 | Reiss ............................ 607/67 |
| 5,370,606 | 12/1994 | Martel et al. ............ 602/21 |
| 5,374,283 | 12/1994 | Flick ............................ 607/152 X |
| 5,381,805 | 1/1995 | Tuckett et al. ............ 128/739 |

OTHER PUBLICATIONS

"Interferential Overview", pp. 1–11.
"High Voltage Pulsed Galvanic Overview", pp. 1–15, Medical Devices, Inc.
"Ferno Ille Introduces Three Modalities In One", one page, Ferno Ille, Wilmington, Ohio.
Pamphlet "Carpal Tunnel Syndrome", Krames Communications, 1987.
Deb Schewe "Carpal Tunnel On the Rise Due to Work Place Habits".
Jane E. Brody, "Epidemic at the Computer: Hand and Arm Injuries" The New York Times.
"Carpal Tunnel Syndrome", MedPRO Month, Oct. 1991, vol. I: No. 10, pp. 154–156.
"That Tingling Sensation May Be Carpal Tunnel Syndrome", PR Newswire, Story 15199, Apr. 15, 1993.
"Are Wrist Braces Safe?", PR Newswire, Story 25631, Jul. 12, 1993.
Jim Szymanski, "Pace", Tacomer, Jul. 8, 1991.
"Exhibit 7 Carpal Tunnel & Repetitive Motion Injuries", National Institute of Occupational Safety and Health.

Primary Examiner—Angela D. Sykes
Assistant Examiner—Stephen Huang
Attorney, Agent, or Firm—Dorsey & Whitney P.L.L.P.

[57] ABSTRACT

A stimulation apparatus is used for treatment of flexing portions of the human body by electrical stimulation. The apparatus has positioning means for firmly holding the flexing portion of the human body. There are two or more stimulation output contacts mounted in the positioning means in predetermined locations relative to each other and the area to be treated with stimulation. A stimulator is electrically connected to the output contacts for introducing electrical stimulation at the output contacts.

19 Claims, 10 Drawing Sheets

APPARATUS FOR ELECTRO-STIMULATION OF FLEXING BODY PORTIONS

BACKGROUND OF THE INVENTION

1. Field of the Invention

This invention generally relates to an apparatus for applying electrical stimulation to reduce pain. In particular, it relates to a stimulation system that can be worn by a patient to reduce pain at joints or other flexing body portions caused by such conditions as carpal tunnel syndrome.

2. Description of the Prior Art

Carpal tunnel syndrome (CTS) is a common and troublesome condition that interferes with the use of the hand. CTS is caused when too much pressure is put on a nerve that runs through a person's wrist. Symptoms of CTS include progressive pain and numbness in the hand. These symptoms occur because the median nerve is compressed as it passes through a narrow tunnel of bone (i.e., carpal tunnel) and ligament at the wrist. The carpal tunnel nerves can be damaged by repetitive motions such as typing or hammering. Nationally, carpal tunnel syndrome annually affects 230,000 workers, costing approximately $3,500 in benefits and rehabilitation per patient.

Neuromuscular stimulation (NMS), transcutaneous electrical nerve stimulation (TENS), and interferential stimulation are three types of electrical stimulation utilized to relieve pain or reduce edema. NMS and TENS, which are the conventional methods of providing electrical stimulation at the surface of the skin, deliver most stimulation to the skin surface directly under an electrode. Adequate pain relief may require careful placement of multiple skin surface electrodes. Moreover, where the pain source is significantly separated from the skin surface, the stimulation (or sufficient stimulation) may not reach the affected area.

Usually, stimulation from NMS and TENS unit is provided via sponge or conductive rubber or elastomeric adhesive electrodes placed at specific locations on the skin. But other approaches have been proposed. U.S. Pat. No. 4,664,118 discloses a glove 10 with a layer of woven metal mesh material to serve as one electrode in an apparatus that provides TENS signals to treat a hand. In this apparatus the entire hand area to be treated is enveloped with the electrically conductive mesh. When the glove acts as one electrode, then a second electrode, such as a metal pad, is required on the patients arm to be able to stimulate the painful hand.

Other delivery methods for the treatment of painful areas with electric stimulation are also known. U.S. Pat. No. 5,067,478 discloses an electrode glove with a layer of conductive material on the shell of the glove. A TENS unit is connected to the electrode glove via a connector. The gloves are used in pairs to deliver electro-massage or electro-acupuncture. A conductive lotion, gel, or warm water is applied to the area of the patient to be treated, and the gloves are placed fiat on that area.

In contrast to TENS and NMS methods, interferential stimulation can concentrate the stimulation deep in the affected tissue. Interferential stimulation uses the constructive and destructive interferences of two slightly different frequencies to produce a beat frequency (see FIG. 12) at locations where both frequencies are present. This interference between the two differing frequencies allows an area to be treated by the stimulation that is typically not effectively reachable with NMS and TENS techniques. U.S. Pat. Nos. 3,895,639 and 4,909,255 both show apparatus that apply interferential stimulation.

Interferential electrical stimulation treatment has been used to relieve the pain experienced by people suffering from carpal tunnel syndrome. Currently, to apply interferential stimulation, a patient is required to place skin electrodes on his hand/arm. The patient is directed to place the four skin electrodes in a criss-cross pattern. The first skin electrode must be placed on the interior side of the wrist. The second skin electrode must be placed on the exterior side of the wrist. The third skin electrode is placed on the back side of the hand and the fourth skin electrode must be placed on the palm at the base of the third metacarpal. Once the skin electrodes are in place, the patient must then correctly connect four wires, one connecting each skin electrode to the stimulation unit. After the patient has managed to place and connect the electrodes correctly, the patient is restricted in movements, because movement of the hand may cause the wires to disconnect or tangle or catch on objects or cause the skin electrodes to fall off the patient's hand/arm. Consequently, this treatment as currently applied is so complex and cumbersome that many patients have difficulty or do not follow their prescribed treatment.

The prior art does not disclose a simple apparatus to allow a patient to apply electric stimulation to the area of carpal tunnel pain. Moreover, the known apparatuses in the prior art make it difficult for a patient to use his/her hands and restrict the ease with which the patient can move about during treatment.

SUMMARY OF THE INVENTION

The present invention is a stimulation apparatus for treatment of flexing portions of the human body by electrical simulation. The apparatus has positioning means for firmly holding the flexing portion of the human body. There are two or more stimulation output contacts mounted in the positioning means in predetermined locations relative to each other and the area to be treated with stimulation. A stimulator is electrically connected to the output contacts for introducing electrical stimulation at the output contacts.

A primary object of this invention is to provide an easy-to-use apparatus to help patients relieve pain in their hands (or other flexing body portions) caused by conditions such as carpal tunnel syndrome. In the hand/wrist version of the present invention, a patient simply puts on a wrist brace positioning means with internal stimulation output contacts and electrodes, connects one connector and turns on the stimulator to begin the treatment. The patient doesn't have to place separate skin electrodes on his/her skin and then connect multiple wires from the stimulator to the skin electrodes. Also, with the present invention, the patient can more easily continue to use his/her hands and move around while receiving the therapy.

The stimulation apparatus of the present invention is particularly adapted to provide an easy-to-use wrist brace stimulator for carpal tunnel syndrome. Once the patient puts on the wrist brace, the skin electrodes are in the predefined, correct positions. Then, once the patient turns on the stimulator, his/her wrist will receive electrical stimulation. Also, while the therapy is being received, the patient can enjoy relatively unimpeded use of his/her hands with little risk of skin electrodes or wires connecting to them becoming loose. Furthermore, the patient can move around freely while receiving the electrical stimulation treatment, because the entire invention is designed to be portable with minimal exposed wires.

DETAILED DESCRIPTION

Figure 1:
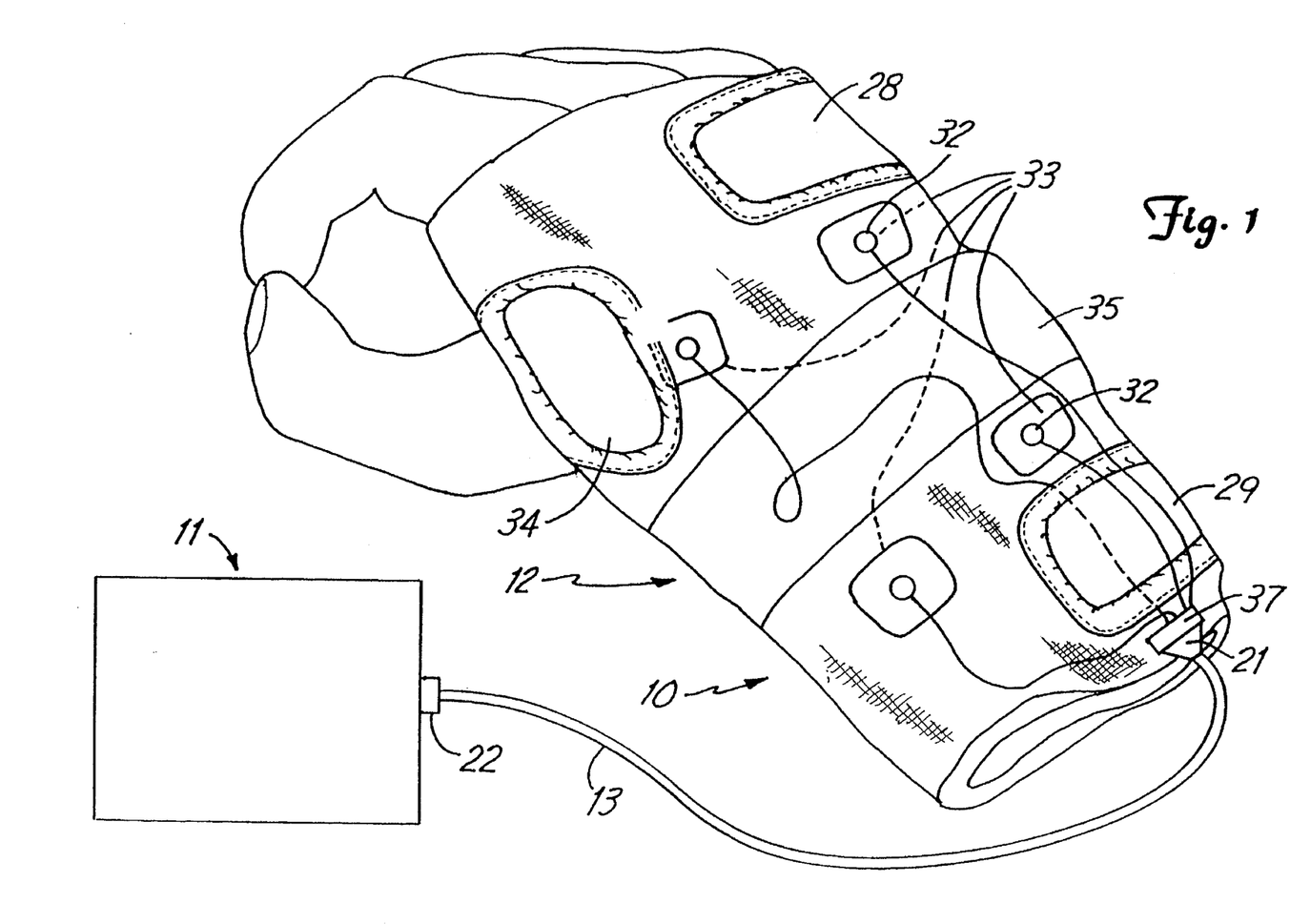
FIG. 1 is a pictorial drawing showing an overview of the present invention in use on a hand.

FIG. 1 shows an overview of a stimulation apparatus 10 in accordance with the present invention. While the apparatus shown is particularly adapted to treat carpal tunnel syndrome at the wrist, this is only an illustrative example. The invention is more generally applicable to other forms of electro-stimulation of flexing body portions.

Figure 2:
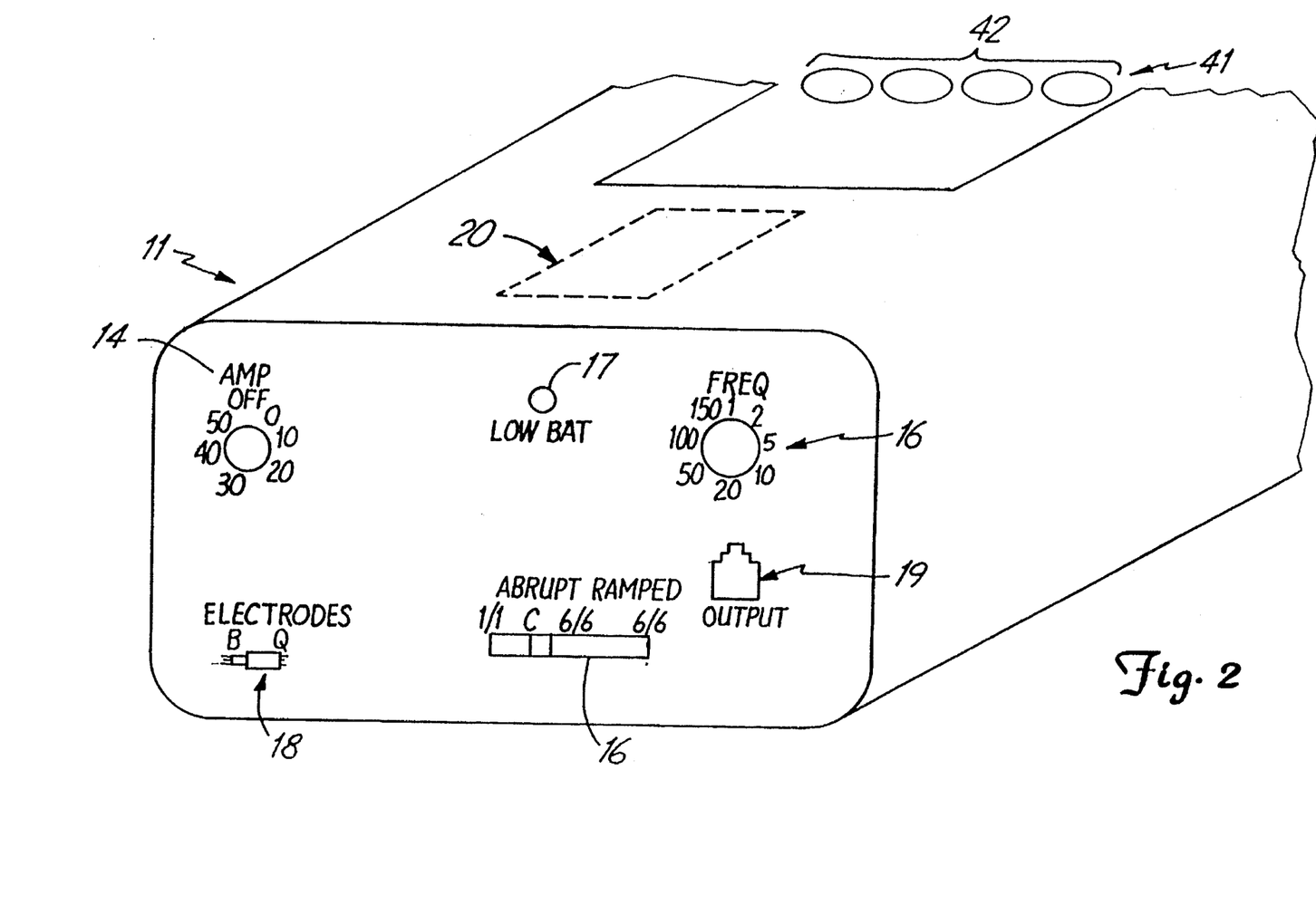
FIG. 2 is a pictorial drawing of a stimulator unit used with the preferred embodiment of the invention.

The stimulation apparatus 10 comprises a stimulator 11 for producing electro-stimulation signals connected to a positioning means 12, in this case a wrist brace, by an umbilical cable 13. The wrist brace 12 has four skin electrodes 33 connected to stimulation contacts or electrode connectors 32 in its interior. These skin electrodes 33 attach to the surface of the hand and wrist in a manner to be described. FIG. 2 shows the control panel and other features of a stimulator 11. This control panel permits control of various features of the electrical stimulation to be delivered, in a manner described below.

Figure 3:
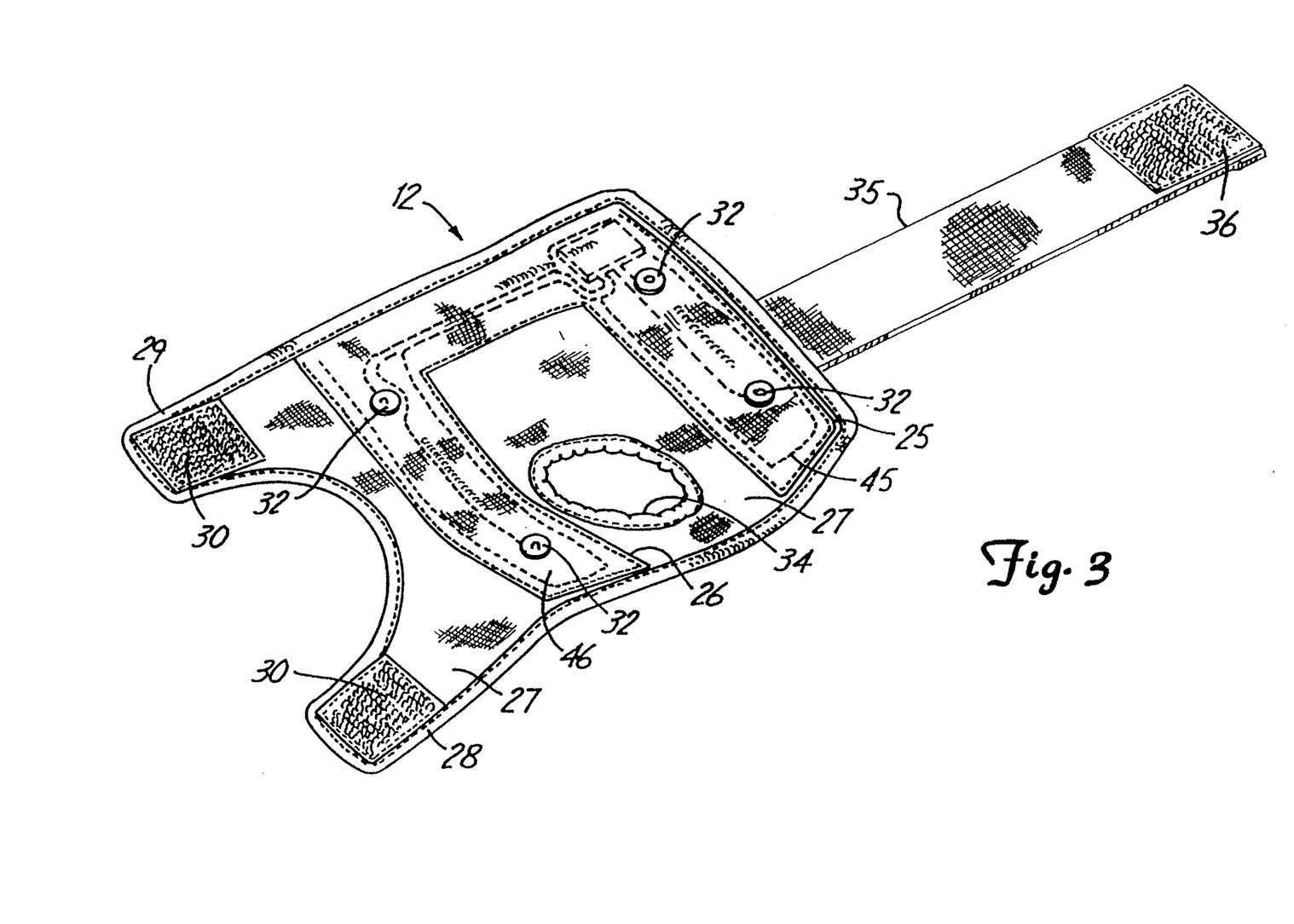
FIG. 3 is a pictorial drawing of the positioning means of the present invention, when laid flat to show its interior surface.
Figure 4:
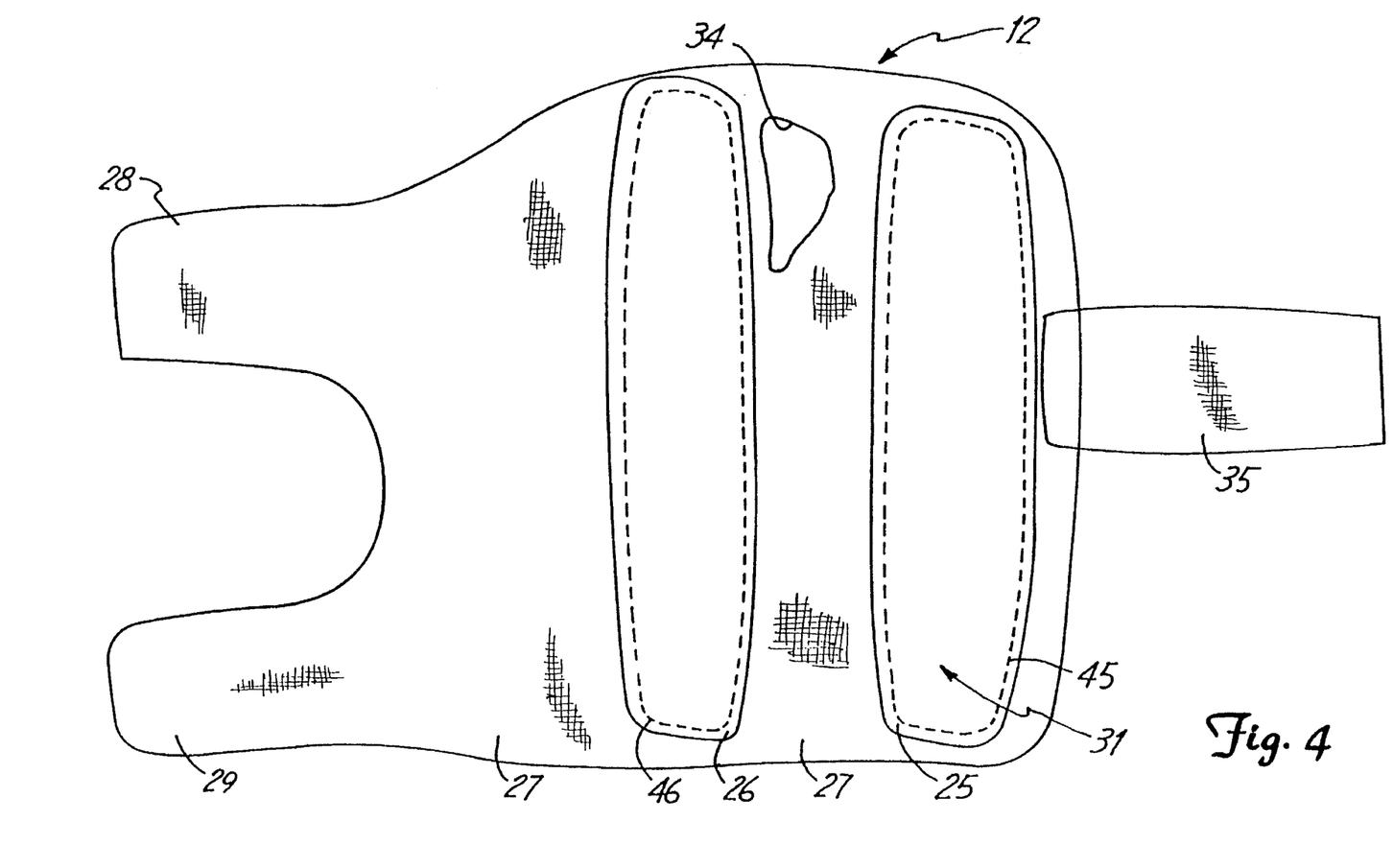
FIG. 4 is a pictorial drawing of the positioning means of the present invention, when laid flat to show its exterior surface.

FIGS. 3 and 4 show a wrist brace positioning means 12 for a right hand/wrist from two points of view. FIG. 3 shows the inner surface of a wrist brace 12, which is the side that contacts the hand/wrist and cannot be seen when the wrist brace 12 is secured on a patient's hand/wrist. FIG. 4 shows the outer surface of the wrist brace 12, which is the side that is visible when the wrist brace 12 is secured on a patient's hand/wrist. The wrist brace 12 has upper and lower internal stiffeners or braces 45, 46, respectively, to restrict motion of the wrist. The braces 45, 46 extend across the flexing portion of the body to substantially limit flexing during stimulation. For the user's comfort, these braces 45, 46 are formed to position the hand in a neutral position and contained within upper 25 and lower 26 brace pads. The upper 25 and lower 26 brace pads are connected with a somewhat elastic mesh fabric 27 with leather backing 48 on portions of the outer surface of the wrist brace 12. (See FIG. 5) A hole 34, which is an opening for a thumb, is constructed between the upper 25 and lower 26 brace pads. The braces 45, 46 support the electrode connectors 32. In the preferred embodiment, there are two electrode connectors 32 on each brace 45, 46.

Figures 5, 6:
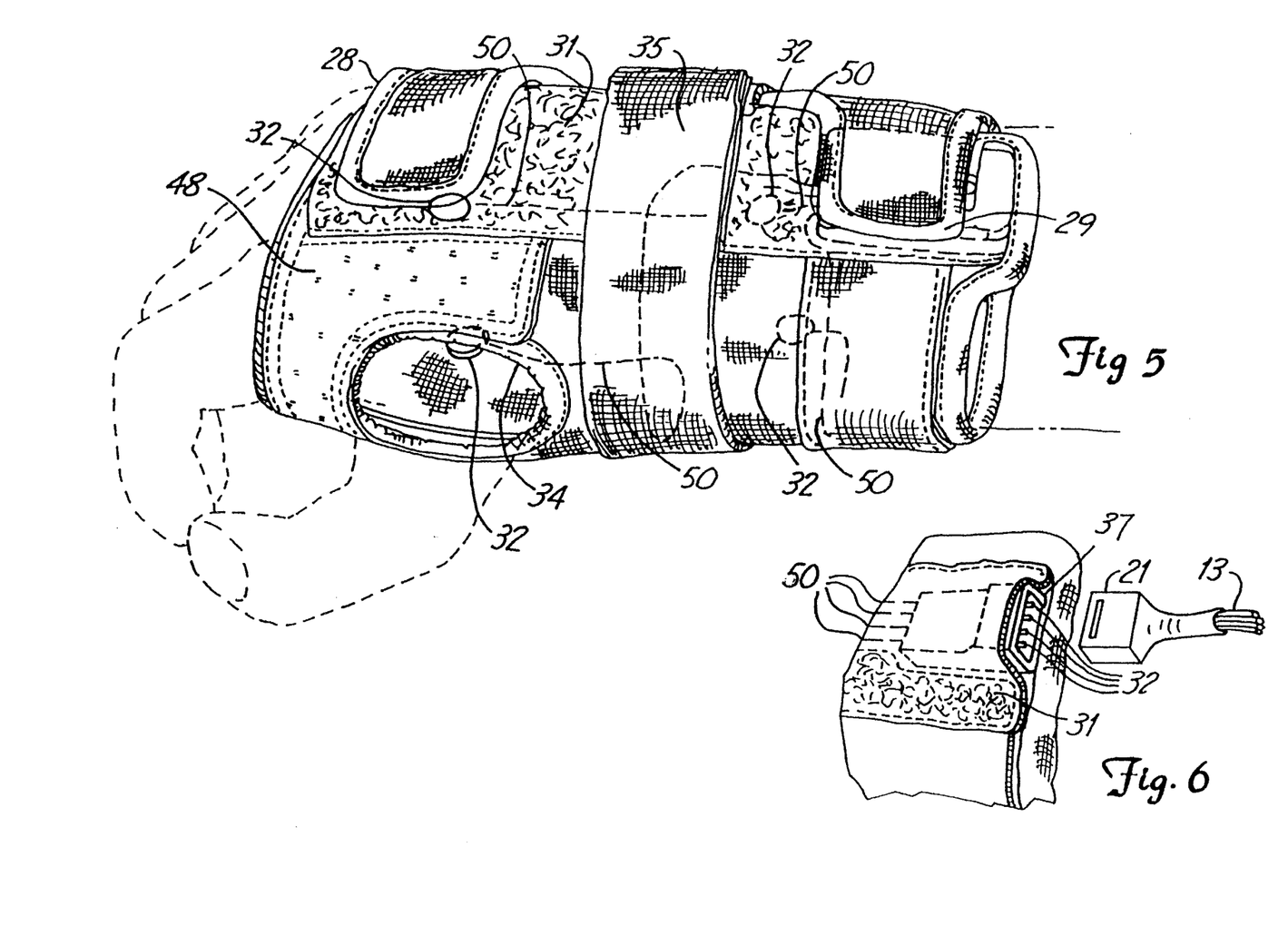
FIG. 5 is a pictorial drawing showing the positioning means on a hand and wrist, including the stimulation output contacts.
FIG. 6 is a pictorial drawing showing the electrical connector components linking the stimulator to the stimulation output contacts in the positioning means employed by the present invention.

As best seen in FIG. 5, the wrist brace 12 is used by wrapping it around the hand/wrist. The means for securing the wrist brace 12 to the hand and the anterior portion of the lower arm is a set of velcro hook pads 30, 36. The fabric 27 adjacent the lower brace pad 26 is cut to have a forward tab 28 and a rearward tab 29. Each tab 28, 29 has an velcro hook pad 30. Also, a web belt 35 with a velcro hook pad 36 extends from the side of the wrist brace 12 adjacent the upper brace pad 25. On the outer surface of the wrist brace 12, a velcro wool pad 31 is attached to the upper brace pad 25. To secure the wrist brace 12 to the hand/wrist, the user inserts his/her thumb into the opening 34 and wraps the wrist brace around the wrist area, with the velcro hook pads 30, 36 being attached to the velcro wool pad 31.

On the inner surface of the upper 25 and lower 26 brace pads are a plurality electrode connectors 32 to which skin electrodes 33 (see FIG. 1) are attached before the user puts on the wrist brace 12. In the preferred embodiment, four electrode connectors 32 are utilized, and one skin electrode 33 is removably attached to each electrode connector 32 by a snap connector arrangement.

In the preferred embodiment, each skin electrode 33 is a thin conductive rubber patch. Each skin electrode is formed as a 1.75"×1.75" square pad with rounded corners. The thickness of the skin electrode is 0.125". The skin electrode has two layers of rubber attached together. On one side of the skin electrode 33 is a snap connector for attachment to the electrode connectors 32 in the wrist brace 12. The other side of the skin electrode 33 has a layer of conductive adhesive on it. This adhesive attaches the skin electrode 33 to a patient's skin when the wrist brace 12 is secured on a patient's hand/arm. When the adhesive is no longer effective or a skin electrode 33 otherwise unusable, a new electrode can be substituted and simply snapped into place.

As shown in FIG. 6, under the velcro wool pad 31, a pin connector 37 is attached to the wrist brace 12. Each of the four electrode connectors 32 has a wire 50 extending to it from a pin in the pin connector 37. Thus each electrode connector 32 is uniquely associated with a particular pin of the connector 37.

The means for connecting the stimulator 11 to the wrist brace 12 is by an umbilical cable 13. The umbilical cable 13 has one connector at each of its ends. In the preferred embodiment, one of the umbilical cable 13 connectors is a multiple receptacle plug connector 21 that is inserted into the pin connector 37 in the wrist brace 12. The other end of the umbilical cable 13 has a connector 22 that resembles a phone jack, which is connected to the output connector 19 (see FIG. 2) of the stimulator 11. Although shown as a separate unit connected as described, with sufficient miniaturization, the stimulator 11 could be made small enough to become an integral part of the wrist brace 12. In that case, the umbilical cable 13 would be unnecessary.

In the preferred embodiment, the wrist brace 12 holds the wrist relatively immobile and in a neutral position, which has therapeutic value to a person suffering from carpal tunnel syndrome. However, the user still has the freedom to use his/her fingers in a relatively unimpeded fashion. In addition, because there is a single cable 20 connecting to the wrist brace 12, and the stimulator 11 is a lightweight pocket-sized unit, the user can easily move about during therapy. Moreover, as explained further below, the wrist brace automatically positions the skin electrodes 33 correctly on the user's hand/wrist helps direct interference stimulation to the carpal tunnel area.

FIG. 2 illustrates a stimulator 11 as used with the present invention. A stimulator 11 is comprised of a signal generator 20, a power source 41 including a power switch present in the amplitude control 14, and an output connector 19. The stimulator 11 also has an amplitude control means which is shown as the amplitude control 14, and a frequency control means which is shown as the frequency control 15. A frequency shifting control means is also present in the stimulator 11, shown as a four-way frequency shifting option switch 16. The stimulator 11 illustrated in FIG. 2, also has a low battery indicator light 17 and, an electrode switch 18.

The signal generator 20 of stimulator 11 produces various waveforms that are provided to the output connector 19. The signal generator 20 can produce a variety of signals including a pulse waveform, a square waveform, and a sawtooth waveform.

The stimulator 11 is a battery powered unit. In the preferred embodiment, the stimulator 11 is powered by 4 AA batteries 42. As mentioned, the power switch for the stimulator 11 is contained in the amplitude control 14. When the amplitude control 14 is turned clockwise to any amplitude setting, the stimulator 11 is switched on. The amplitude control 14 allows the user to determine the strength of the electrical stimulation that is to be applied by the stimulator 11.

In the preferred embodiment, the stimulator 11 delivers interferential stimulation by providing signals of two slightly differing frequencies at each of two opposing sets of electrodes 32. To deliver the interferential signal most effectively to the carpal tunnel area, four stimulation contacts are used, as described below.

The frequency control 15 allows the user to control the rate at which the waveforms are delivered by the stimulator 11.

The frequency shifting switch 16 controls the pattern of frequency shifting in a rhythmic manner. This feature is discussed in the context of an interferential stimulation pattern. The "1/1 abrupt", "C", "6/6 abrupt", and "6/6 ramped" settings illustrated in FIG. 2, provide different levels of shifting. "C" stands for operating the stimulation unit 11 in a continuous mode. In the continuous mode, the stimulation unit 11 will continuously produce the single interference frequency set by the frequency control 15. The range of available interference frequencies is 1 to 150 Hz, derived from a fixed carrier frequency of 4000 Hz and an adjustable frequency of 4001 to 4150 Hz (nominal values).

In the other options, the interference frequency changes over time from −30% to +60% of the set frequency value. For example, with the frequency control 15 set at 100 Hz, the interference frequency would shift repeatedly from 70 Hz to 160 Hz. During interferential stimulation, this shift in frequency occurs because of the constructive and destructive interference of the waves of differing frequencies flowing between the skin electrodes 33. The frequency shift designations "1/1 abrupt," "6/6 abrupt", and "6/6 ramped" indicate how long the frequency stays at each shifted value and whether it makes the transition from one frequency to another quickly or slowly.

When set at "1/1 abrupt" with the frequency control 15 set at 100 Hz, the interference frequency would be at 70 Hz for one second, then shift abruptly to 160 Hz for one second, then back to 70 Hz for one second. This pattern will be repeated as long as the frequency shift is in the "1/1 abrupt" mode. The frequency shift option "6/6 abrupt" is identical to "1/1 abrupt" except that each interference frequency is held for six seconds instead of one second.

If the frequency control 15 is set at 100 Hz and the frequency shift option is set at "6/6 ramped", then the frequency shifts from 70 Hz to 160 Hz gradually over a six-second period, rather than quickly. In the following six seconds the frequency shifts gradually from 160 Hz back to 70 Hz. The cycle is then repeated.

In the preferred embodiment, the "Electrodes" switch 18 allows selection of either bipolar or quadrapolar stimulation. Quadrapolar stimulation, using four electrodes placed in a criss-cross pattern, epitomizes interferential therapy and is the preferred application technique. With bipolar stimulation only two electrodes are necessary, because the carrier and interfering frequency are mixed within the stimulator 11 itself. Both quadrapolar and bipolar stimulation benefit from the low impedance encountered by medium frequencies. In addition, quadrapolar stimulation capitalizes on the beat frequency produced at the intersection between the carrier frequency and the adjustable (interfering) frequency deep within tissue. The intensity of the beat deep within tissue is considerably larger with quadrapolar stimulation than with bipolar stimulation.

A suitable commercially available stimulator 11 with the preceding features is the IF II Interferential Stimulation System from Medical Devices, Inc. of St. Paul, Minn.

Figure 7:
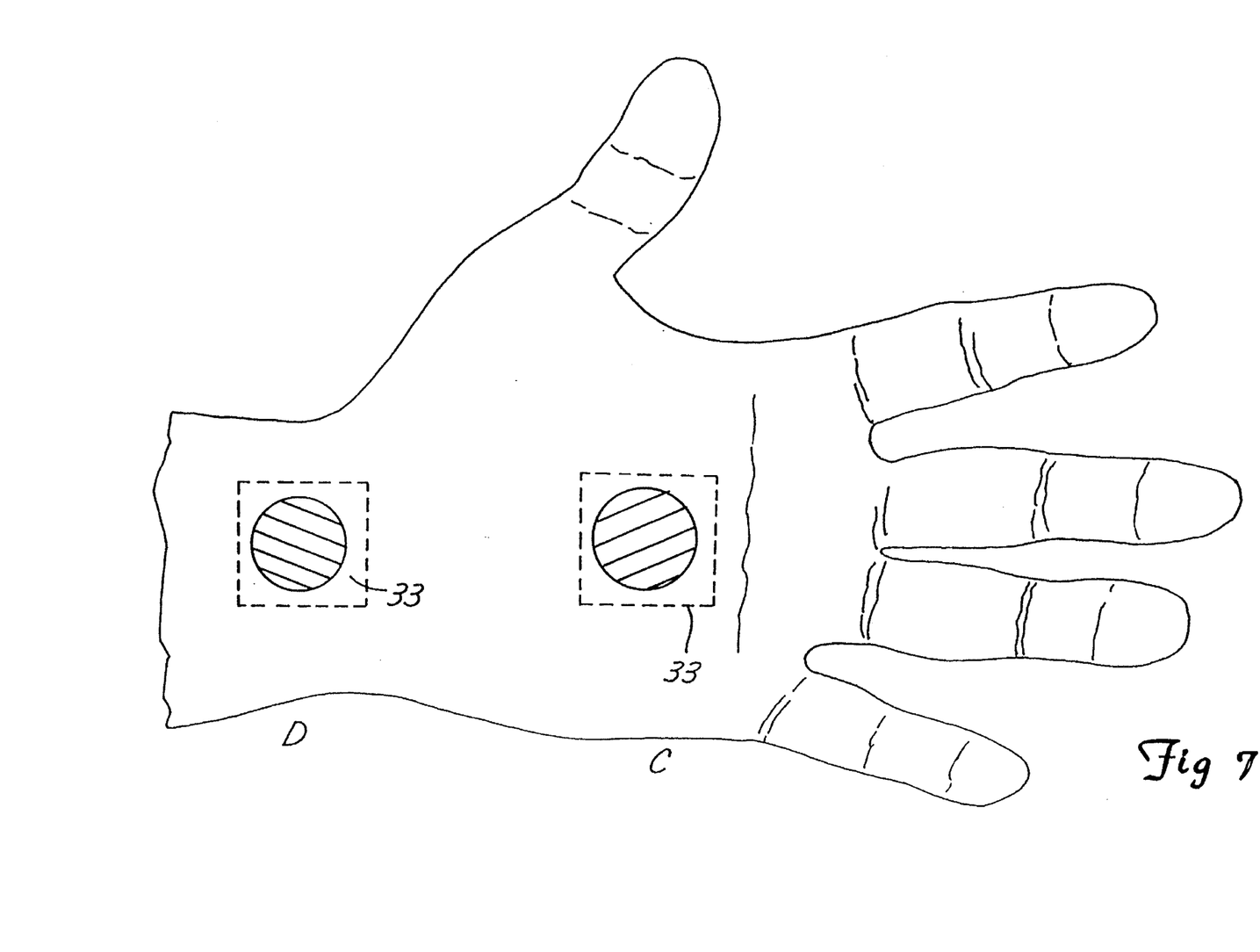
FIG. 7 illustrates the stimulation points addressed by the present invention on the interior of a hand and wrist.
Figure 8:
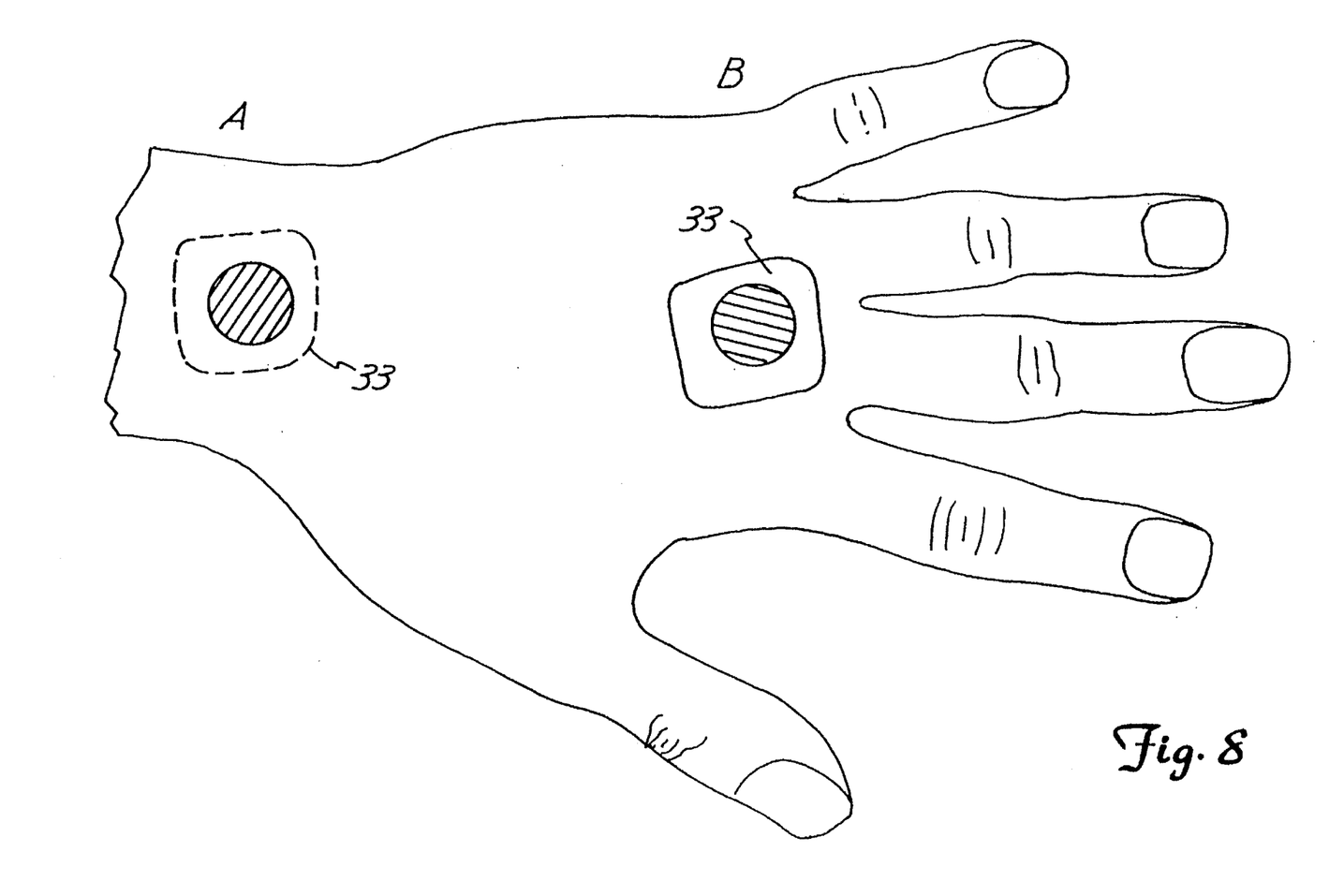
FIG. 8 illustrates the stimulation points addressed by the present invention on the exterior of a hand and wrist.

Ideally, the stimulator 11 used in the present invention can provide neuromuscular stimulation (NMS) or transcutaneous electrical nerve stimulation (TENS), in addition to interferential stimulation. However, the preferred embodiment utilizes interferential stimulation. For optimal interferential stimulation of the carpal tunnel area of the wrist, four stimulation points or contacts in specified relation to the wrist are used. These are shown in FIGS. 7 and 8, as follows a first point (D) at an anterior, inner portion of the wrist;

a second point (A) at an anterior, outer portion of the wrist;

a third point (C) at the palm of the hand adjacent the wrist; and a fourth point (B) at the back of the hand adjacent the wrist.

For proper interferential stimulation within the wrist tissue, the appropriate electrical stimulation must be delivered to each of these points.

Figure 9:
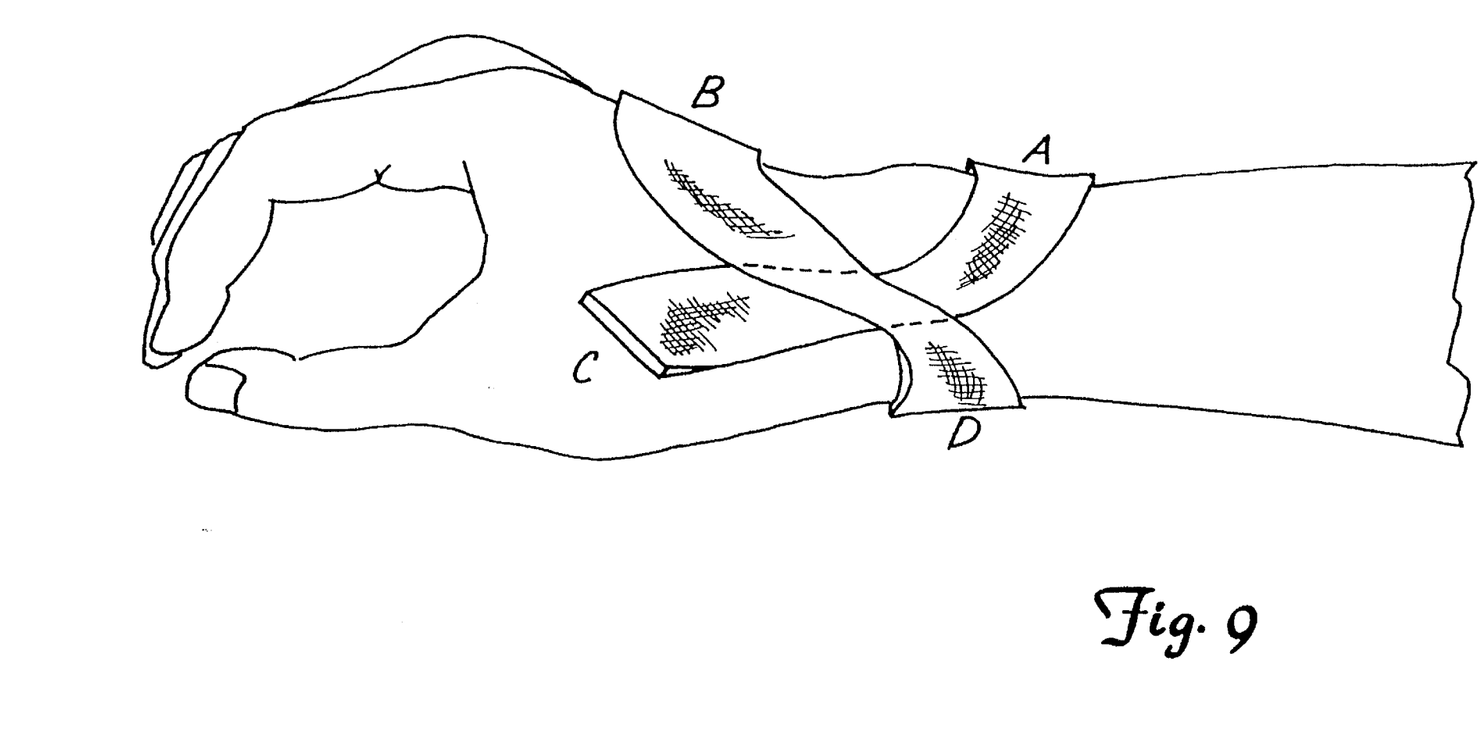
FIG. 9 shows an interferential stimulation pattern that can be produced with the present invention.

When the wrist brace 12 is secured on a patient's hand/wrist with skin electrodes 33 attached to each of the output contacts 32, the skin electrodes 33 are brought into contact with the patient's hand and wrist. As seen in FIG. 8, a skin electrode 33 is automatically positioned at point A on the wrist and a skin electrode 33 is automatically positioned at point B on the dorsal portion of the patient's hand. As shown in FIG. 9, skin electrodes 33 are automatically positioned on the palm (point C) and interior wrist areas (point D) of the patient's hand. Not only are the electrodes 33 properly positioned by virtue of their predetermined locations relative to each other and the area to be treated, they are held securely in place by their containment within the wrist brace 12.

Figure 12:
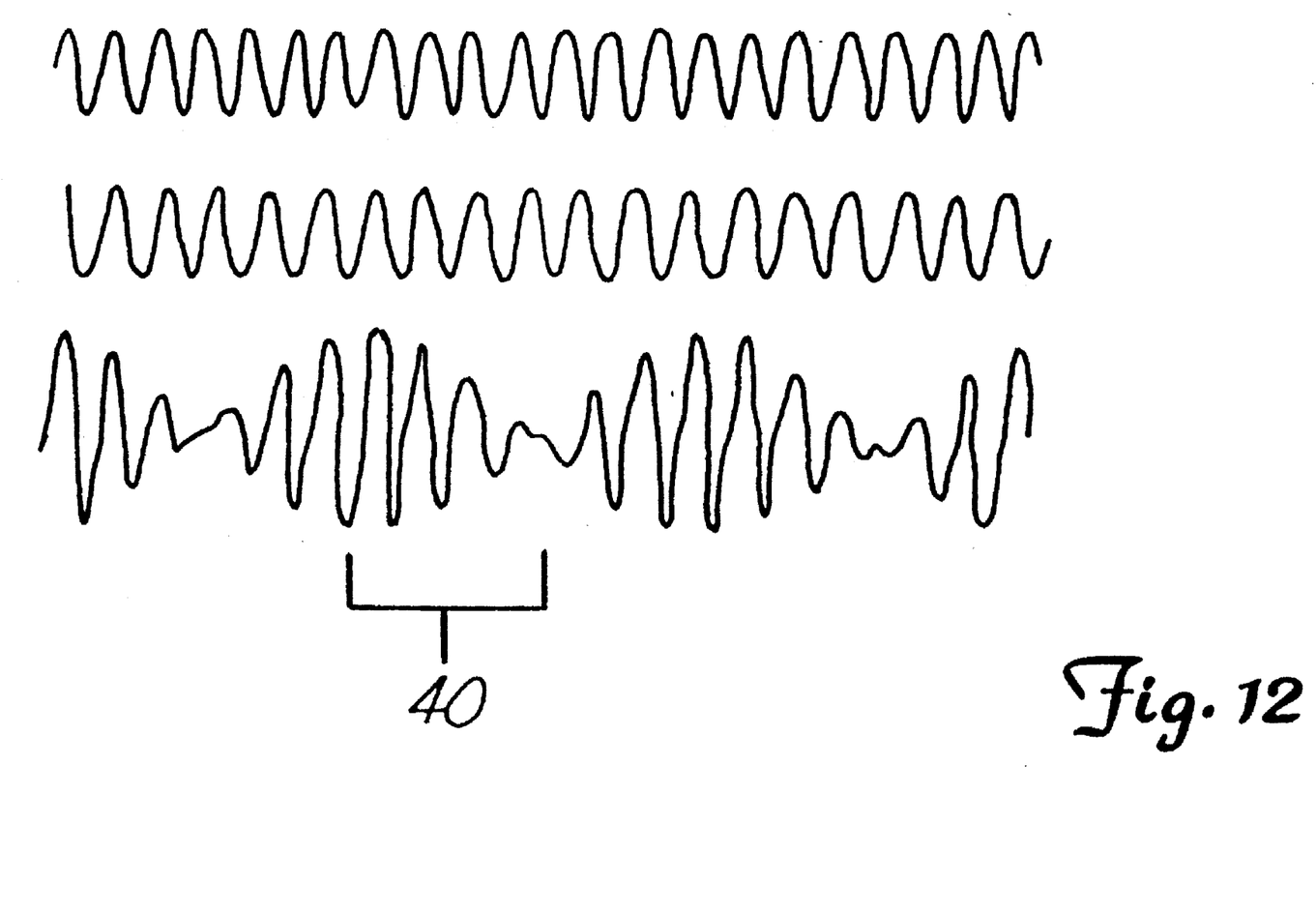
FIG. 12 shows two wave-forms of stimulation signals with slightly different frequencies and the resulting interference signal.

When the electrodes switch 18 is set to quadrapolar stimulation and the stimulator 11 is turned on, the signal generator 20 produces a series of waveforms. The waveforms flow from the output connector 19 through an umbilical cable 13 which carries the waveforms to the electrode multi-pin connector 37 at the wrist brace 12. The waveforms then travel through wires 50 in the wrist brace 12 to the electrode connectors 32 and the skin electrodes 33. One waveform flows between the skin electrode 33 at point A and the skin electrode 33 at point C; another waveform flows between the skin electrode 33 at point B and the skin electrode 33 at point D. Because interferential stimulation is used, the two waveforms will interfere constructively and destructively within the tissue and cause a beat frequency 40 as illustrated in FIG. 12. This type of sensory stimulation has been found helpful to control pain. It is believed that this effect is achieved because non-painful sensory stimulation interferes with the transmission of pain messages at the spinal cord level, preventing pain signals from reaching the brain.

With interferential stimulation a criss-cross pattern is utilized to bracket the nerve, because a secondary foci of stimulation will occur along lines at 45° angles to the lines connecting each pair of electrodes. With TENS, by contrast, the clinician will usually place electrodes along a nerve path, to passing current along the nerve track. It should still be noted that with interferential stimulation, the main focus of stimulation will be at the intersection point of the straight lines connecting each pair of electrodes from a channel. Because of the spatial dispersion of the interference pattern within the hand/wrist tissue, the positioning means plays another role. In holding the flexing body portion in one position, it provides a consistent tissue configuration for the interference pattern.

Figures 10, 11:
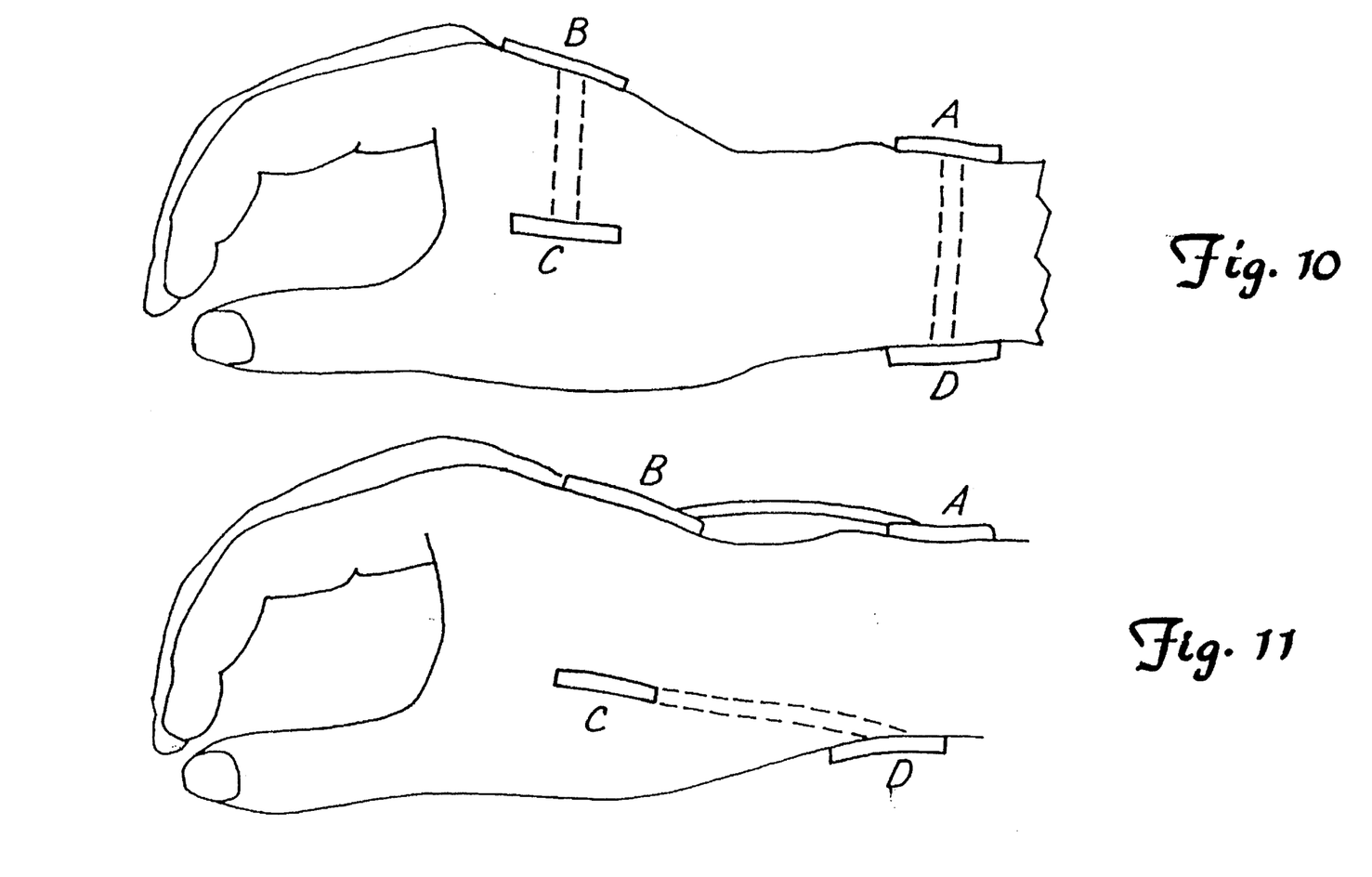
FIGS. 10 and 11 show alternative stimulation patterns that can be produced by the present invention.

Although the criss-cross pattern is the preferred method, this invention may be used to apply stimulation between any two electrodes supported by the wrist brace 12. As illustrated in FIGS. 10 and 11, the waveforms can travel between any suitably connected pair of electrodes. Consequently, the apparatus disclosed in this application is flexible in its ability to deliver stimulation to different parts of the hand/wrist tissue.

In another embodiment of the present invention, the stimulator unit 11 may be simplified so that the patient may only adjust the amplitude. All other parameters such as the frequency are not available for patient control.

Although the present invention has been shown and described with respect to preferred embodiments, various changes and modifications that are obvious to a person skilled in the art to which the invention pertains are deemed to lie within the spirit and scope of the invention as defined by the following claims.

What is claimed is:

1. An apparatus for introducing electrical stimulation into a flexing portion of a human body, comprising:

positioning means for firmly holding said flexing portion in a predetermined position so that said flexing portion is held in substantial immobility;

two or more stimulation contacts mounted in the positioning means in predetermined locations relative to each other and an area to be treated with stimulation so that the electrical stimulation bridges said flexing portion; and stimulator means electrically connected to the stimulation contacts for introducing electrical stimulation at the stimulation contacts.

2. The apparatus as recited in claim 1 wherein the positioning means is a brace that firmly holds a wrist and hand with a palm and a back in a position of substantial immobility.

3. The apparatus as recited in claim 2 wherein the two or more stimulation contacts comprise four stimulation contacts as follows:

a first contact for positioning at an anterior, inner portion of the wrist;

a second contact for positioning at an anterior, outer portion of the wrist;

a third contact for positioning at the palm of the hand adjacent the wrist; and a fourth contact for positioning at the back of the hand adjacent the wrist.

4. The apparatus as recited in claim 3 wherein the stimulator means is an interferential stimulator.

5. The apparatus as recited in claim 4 wherein the stimulator is connected to the stimulation contacts so that the first and fourth contacts are part of a circuit delivering one channel of stimulus of a first specified frequency and the second and third contacts are part of a circuit delivering a second channel of stimulus of a second specified frequency with an interference relationship to the first frequency.

6. The apparatus as recited in claim 1 further comprising a skin electrode associated with and placed in electrically conductive relationship with each of said stimulation contacts.

7. The apparatus as recited in claim 1 wherein said stimulator means comprises a signal generator;

a power source including a switch; and an output connector.

8. The apparatus as recited in claim 7 wherein said signal generator comprises waveform production means for producing various waveforms.

9. The apparatus as recited in claim 8 wherein one of said various waveforms is a pulse waveform.

10. The apparatus as recited in claim 8 wherein one of said various waveforms is a square waveform.

11. The apparatus as recited in claim 8 wherein one of said various waveforms is a sawtooth waveform.

12. The apparatus as recited in claim 1 wherein said stimulator means further comprises an amplitude control means for controlling amplitude of the electrical stimulation.

13. The apparatus as recited in claim 8 wherein said stimulator means further comprises a frequency control means for controlling the rate at which the waveforms are delivered by said stimulator.

14. The apparatus as recited in claim 1 wherein said stimulator means further comprises means for generating a carrier frequency and an adjustable interference frequency; and a frequency shifting control means for controlling in a predetermined manner changes in the adjustable interference frequency.

15. The apparatus as recited in claim 1 wherein the positioning means comprises a brace that contains stiffeners that are adapted to extend across the flexing portion of the body to substantially limit flexing during stimulation.

16. An apparatus for introducing electrical stimulation into a hand with a palm and a back, and a wrist portion of a human body, comprising:

a wrist brace for firmly holding said hand and wrist portion in a predetermined position so that said hand and wrist portion are held in substantial immobility;

two or more stimulation contacts mounted in the wrist brace in predetermined locations relative to each other and the hand and wrist portion to be treated with stimulation so that the electrical stimulation bridges the hand and the wrist portion;

two or more skin electrodes adapted to be with each skin electrode attached to one of said two or more stimulation contacts and each skin electrode adapted to be attached to said surface of hand and wrist portion; and a stimulator electrically connected to the stimulation contacts for introducing electrical stimulation to the hand and wrist portion through the stimulation contacts and the skin electrodes.

17. An apparatus for introducing electrical stimulation into a hand, having a palm and a back, and a wrist portion of a human body, comprising:

a brace for firmly holding said wrist and hand in a position of substantial immobility;

four stimulation contacts mounted in said brace such that:
a first contact is positioned at an anterior, inner portion of the wrist;
a second contact is positioned at an anterior, outer portion of the wrist;
a third contact is positioned at the palm of the hand adjacent the wrist;
a fourth contact is positioned at the back portion of the hand adjacent the wrist; and stimulator means electrically connected to the stimulation contacts for introducing electrical stimulation at the stimulation contacts.

18. The apparatus is recited in claim 17, wherein the stimulator means is an interferential stimulator.

19. The apparatus as recited in claim 18, wherein the stimulator is connected to the stimulation contacts so that the first and fourth contacts are part of a circuit delivering one channel of stimulus of a first specified frequency and the second and third contacts are part of a circuit delivering a second channel of stimulus of a second specified frequency with an interference relationship to the first frequency.

* * * * *